United States Patent
Pearce

(10) Patent No.: US 8,075,780 B2
(45) Date of Patent: Dec. 13, 2011

(54) PURIFICATION AND CONCENTRATION OF SYNTHETIC BIOLOGICAL MOLECULES

(75) Inventor: Richard James Pearce, Swampscott, MA (US)

(73) Assignee: Millipore Corporation, Billerica, MA (US)

( * ) Notice: Subject to any disclaimer, the term of this patent is extended or adjusted under 35 U.S.C. 154(b) by 258 days.

(21) Appl. No.: 10/981,328

(22) Filed: Nov. 4, 2004

(65) Prior Publication Data

US 2005/0112755 A1    May 26, 2005

Related U.S. Application Data

(60) Provisional application No. 60/524,682, filed on Nov. 24, 2003.

(51) Int. Cl.
*B01D 61/18* (2006.01)
*B01D 61/14* (2006.01)

(52) U.S. Cl. ........ 210/651; 210/653; 210/654; 210/655; 210/321.75; 210/500.27; 204/540

(58) Field of Classification Search .............. 204/540, 204/541, 544, 548, 630, 644, 543; 210/651–655, 210/321.72–321.75, 500.27
See application file for complete search history.

(56) References Cited

U.S. PATENT DOCUMENTS

| 4,824,568 A | 4/1989 | Allegrezza et al. |
| 5,049,282 A | 9/1991 | Linder et al. |
| 5,437,774 A * | 8/1995 | Laustsen .................. 204/518 |
| 5,997,745 A | 12/1999 | Tonelli et al. |
| 7,001,550 B2 * | 2/2006 | van Reis .................. 264/48 |
| 2003/0178368 A1 | 9/2003 | Van Reis |

FOREIGN PATENT DOCUMENTS

| JP | 58-198299 A | 11/1983 |
| JP | 03193121 | 11/1991 |
| JP | 2000-513580 A | 10/2000 |
| JP | 2002-543971 A | 12/2002 |
| WO | 1998/015681 A1 | 4/1998 |

OTHER PUBLICATIONS

Japanese Patent Abstract for JP 63185403 A Published on Aug. 1, 1998 to Toray Ind. Inc.*
Childress A E et al, "Effect of humic substances and anionic surfactants on the surface charge and performance of reverse osmosis membranes", Desalination Elsevier Scientific Publishing Co, Amsterdam NL, vol. 118, No. 1-3, Sep. 20, 1998 p. 167-174.
Li S-L et al, "Separation of l-glutamine from fermentation broth by nanofiltration", Journal of Membrane Science, Elsevier Scientific Publ Co, Amsterdam NL, vol. 222, No. 1-2, Sep. 1, 2003, pp. 191-201.
Van Reis R et al, "High-performance tangential flow filtration using charged membranes", Journal of Membrane Science, Elsevier Science, Amsterdam NL, vol. 159, No. 1-2, Jul. 1, 1999, pp. 133-142.
European Search Report received for EP Patent Application No. 04257246.1 mailed on Mar. 3, 2005, 4 pages.

* cited by examiner

*Primary Examiner* — Arun S Phasge

(57) ABSTRACT

The present invention is an ultrafiltration (UF) membrane having a nominal molecular weight cut off (NMWCO) of from about 0.5 KD to about 10 KD wherein the membrane surfaces have a charge that is either positive or negative. The present invention is also a method of using the charged UF membrane to purify and concentrate synthetic biological molecules by using the charged surface either to repel the synthetic biomolecules retaining them in the retentate or to attract the synthetic biomolecules preferentially for filtration through the membrane.

27 Claims, 3 Drawing Sheets

PURIFICATION AND CONCENTRATION OF SYNTHETIC BIOLOGICAL MOLECULES

CROSS REFERENCE TO RELATED APPLICATIONS

This application claims the benefit of U.S. Provisional Patent Application No. 60/524,682, filed on Nov. 24, 2003. The entire contents incorporated herewith.

BACKGROUND OF THE INVENTION

The present invention relates to the purification and concentration of synthetically manufactured biological molecules. More particularly, it relates to the purification and concentration of synthetically manufactured biological molecules, such as oligonucleotides, synthetic DNA and synthetic RNA, by ultrafiltration.

Synthetic biological molecules, such as oligonucleotides, synthetic DNA and synthetic RNA are being investigated as therapeutic agents. These molecules would be used in lieu of natural or recombinant molecules. There are a number of reasons for doing so. Some molecules just don't exist in nature or for some reason can't be replicated yet using recombinant technologies. Synthetic synthesis can overcome this limitation. Often, there are variants of eth same molecule. Synthetics allow one to custom tailor the molecule to its desired form. Lastly, synthetics and their manufacture are often less expense to manufacture and often avoid the issues of handling biohazards.

These molecules are typically formed by synthetic chemical precursors and are assembled on various solid substrates within synthesizers.

After formation, they need to be purified and in many instances concentrated, either for further processing or formulation.

The molecules generally are cleared from their solid support and then subjected to a purification step such as ultrafiltration or chromatographic capture to remove impurities.

The desired molecules are relatively small, typically having a molecular weight from about 0.5 to about 5 Kilo Daltons (KD).

As such, they are difficult to purify and concentrate by ultrafiltration as they are often about the same size as the membrane pore used to retain them. This results in relatively low yields of product being obtained Additionally, the membranes, having such small pore sizes, suffer from low fluxes and processing times can be measured in hours. This drives up the cost of the process as well as placing an undue burden on the membranes and the system components.

Due to this limitation, ultrafiltration is not widely accepted for this application and one uses chromatography, precipitation or distillation techniques to purify and concentrate these molecules.

These processes have their own disadvantages. They are biotech-based and most times, especially process scale chromatography, are more expensive than ultrafiltration. The precipitation often introduces an additional chemical that needs to be removed. Distillation may adversely affect the molecules especially any that are heat sensitive.

The present invention provides the means for enabling ultrafiltration in this application.

SUMMARY OF THE INVENTION

The present invention is an ultrafiltration (UF) membrane having a nominal molecular weight cut off (NMWCO) of from about 0.5 KD to about 10 KD wherein the membrane surfaces have a charge that is either positive or negative. The present invention is also a method of using the charged UF membrane to purify and concentrate synthetic biological molecules by using the charged surface either to repel the synthetic biomolecules retaining them in the retentate or to attract the synthetic biomolecules preferentially for filtration through the membrane.

The present invention allows for the removal of small molecular weight impurities, thereby reducing the need for chromatography or other steps to achieve similar purification levels. It also allows for the use of larger pored membranes, thereby increasing flux and improving process speed and economics and creating greater yields of product.

DETAILED DESCRIPTION OF THE INVENTION

The present invention relates to the use of one or more charged, positive or negative, membranes to purify and/or concentrate synthetic biomolecules such as oligonucleotides, synthetic DNA and synthetic RNA.

As mentioned above, the problem with ultrafiltration in the processing of synthetic biomolecules is two-fold. First, the molecules themselves are small, typically from about 0.5 to about 5 KD in size. This requires the use of very tight UF membranes. Even then, often these molecules are the same size as the openings in the membranes. As a result, often the target molecule will pass through the membrane, resulting in lower yields of that molecule. Secondly, such tight membranes have very low flux characteristics, meaning that little material passes through them in a given time. This increases the amount of time necessary to process a given amount of fluid over a larger pored membrane. Additionally, the low flux can create higher back and transmembrane pressures on the membrane and system, which is also detrimental.

The present invention uses one or more UF membranes that contain either a positive or negative charge.

Preferably, the membrane contains the same charge as the target molecule. As same charges repel each other, the membrane repels the target molecule away from its surface. This phenomenon can be used to one's advantage. It allows one to use a membrane with a higher NMWCO than the target molecule to achieve higher flux and greater throughput while also increasing yields of the target molecule.

The similarly charged target molecules behave as if they are larger than they actually are due to the charge they and the membrane(s) have. Thus, even though physically the target molecules could pass through the membrane, their like charge prevents this from happening.

Additionally, the smaller impurities still pass through the membrane even when they have the like charge due to their smaller size and the force of filtration which is greater than the force of charge repulsion.

Figure 1:
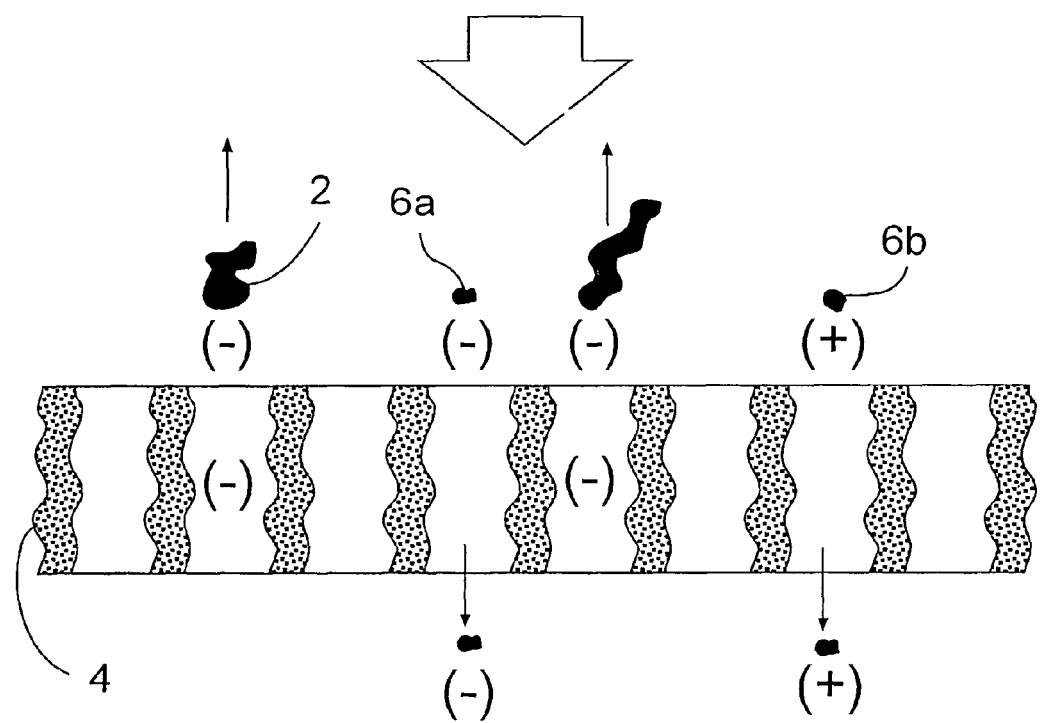
FIG. 1 shows a cross-sectional cut away of a membrane of the present invention in use.

FIG. 1 shows a diagrammatic representation of a membrane and molecule according to the present invention. In this embodiment, the target molecule 2 is assumed to be negative and the surface of the membrane 4 is made to have a negative charge as well. The impurities 6A and B may be negative or positive. As shown, as the fluid containing the target molecule passes over the membrane 4 the molecules 2 are repelled from the membrane 4 due to their like charges and are retained in the retentate. The impurities due to their size and the filtration force, whether of like or different charge, pass through the membrane to the filtrate side.

Figure 2:
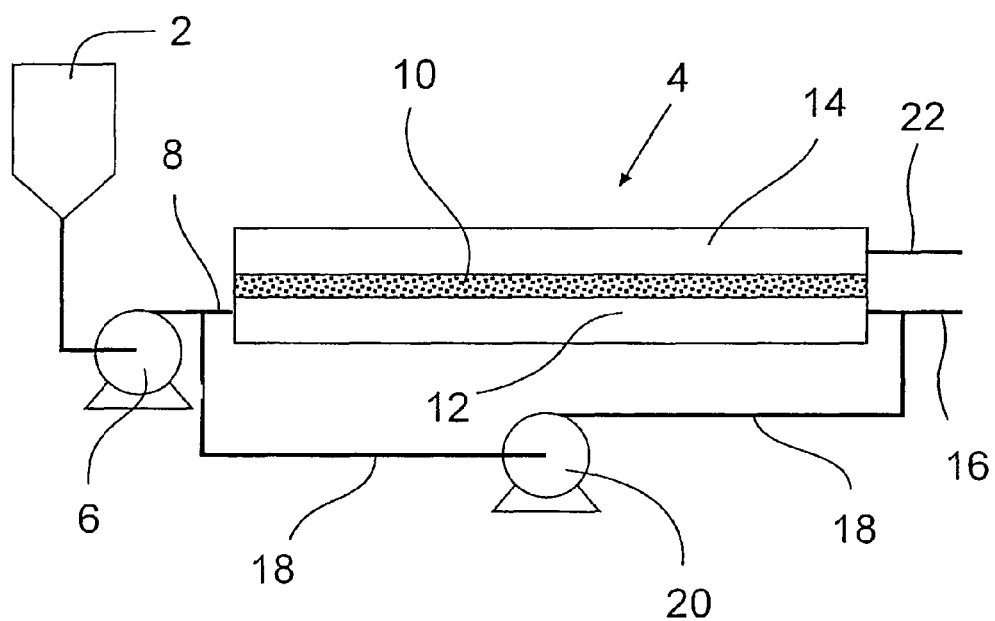
FIG. 2 shows a system according to the present invention.

FIG. 2 shows a system according to the present invention for purifying and/or concentrating synthetic biomolecules. A source 20 of the biomolecules is in the fluid communication with a filter holder 22. In this embodiment, the system is run in tangential flow mode (TFF). A pump 24 is located downstream from the source 20. Its outlet 26 is connected to the inlet 28 of the holder 22. Downstream is one or more membranes 30 that separate the holder 22 into an upstream compartment 32 and a downstream compartment 34. Fluid and any solids or solvents reaching the downstream compartment 34 must first pass through the one or more membranes 30. The upstream compartment 32 also has a retentate outlet 36. Optionally, as shown, the retentate outlet 36 also has a return loop 38 in fluid communication upstream of the inlet 28 to return retentate back to the system if desired. Also shown is an optional retentate pump 40. As shown, the return loop 38 is between the pump 24 and the inlet 28 of the holder. Alternatively, it may return to the source 20 or any point between the source 20 and the inlet 28. Also shown is the filtrate outlet 42 located in the downstream chamber.

In operation, fluid from the source enters the inlet 28 of the holder 22 and flows across the one or more membranes 30. Fluid and either impurities or the target molecule pass through them to the downstream compartment 34. It is preferred that the target molecule and the membrane(s) have the like charge.

Figure 3:
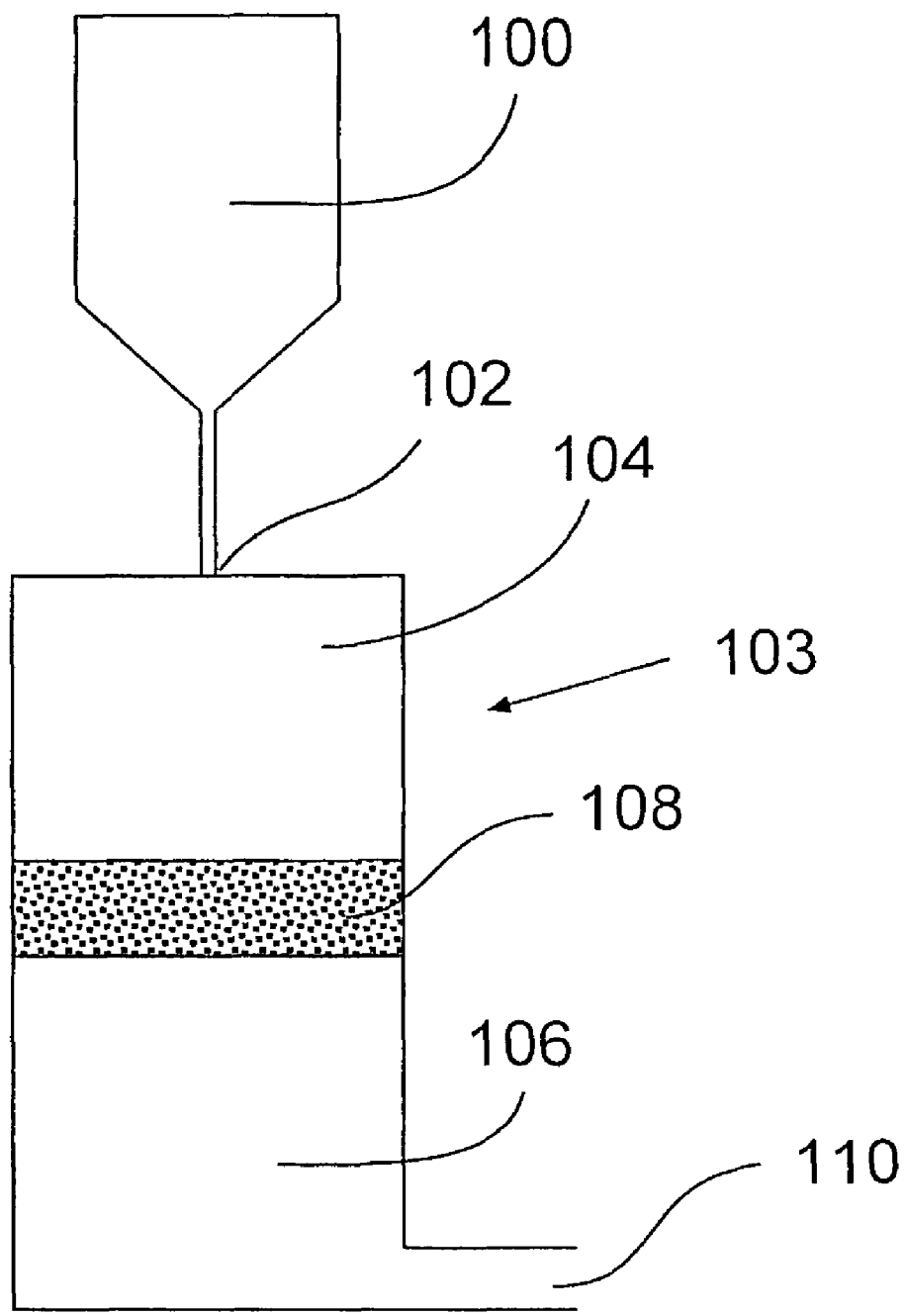
FIG. 3 shows a second system of the present invention.

FIG. 3 shows a normal flow system of the invention. The source 100 is in fluid communication with the inlet 102 of the filter device 103. Fluid enters the inlet 102 into an upstream compartment 104 that is separated from a downstream compartment 106 by an ultrafilter membrane 108. Any fluid, solid or solute, reaching the downstream compartment 106 must have passed through the membrane 108. The filtrate then exits the device through outlet 110.

Alternatively, the embodiment of FIG. 2 can function in a normal flow manner by eliminating the optional return loop 18 and pump 20.

Two characteristics of the selected membrane or filter are important to note in this regard, sieving and permeability.

Sieving is the ratio of concentration of desired molecule downstream of the filter compared to the concentration of molecule upstream of the filter after filtration. The higher the value the greater the amount of the desired molecule passes through the filter. Thus a high value is indicative of the molecule readily passing through the filter. Conversely a low value is indicative of most of the molecule being retained upstream of the filter. Where it is desired to keep the molecule upstream (retentate side) of the filter and the molecule of interest and the membrane have the same charge a low sieving value is desirable. Conversely when it is desired to have the molecule in the filtrate (passing through the membrane or filter) a high value is desirable.

Permeability is the filtration rate of the membrane or filter. It is largely determined by the pore size, percentage porosity and thickness of the membrane and the viscosity and concentration of the solution being filtered. For an uncharged membrane permeability decreases as sieving decreases. For a charged membrane according to the present invention, the sieving improves over that of the uncharged membrane (the sieving value either goes lower if the molecule is in the retentate or goes higher if the molecule is in the filtrate) while the permeability remains the same or is only slightly decreased such that the combination of sieving and permeability is overall improved as compared to an uncharged system. For example, where the molecule is the same charge as the membrane and thus kept in the retentate, the improvement is observed as a lower sieving value accompanied with no or little reduction in permeability. According to the present invention, the improvement in sieving should be at least 1.5 fold, alternatively, at least 2 fold, alternatively at least 5 fold, preferably at 10 fold, more preferably at 50 fold better than the sieving value achieved with an uncharged membrane or filter.

Any ultrafiltration membrane that is capable of carrying a desired charge at least under operating conditions is useful in the present invention. Such membranes are well known in the art.

For example, U.S. 2003/0178368 A1 teaches how to make a charged cellulosic filtration membrane by covalently modifying the membrane's surfaces with a charged compound or a compound capable of being chemically modified to possess a charge. For example, a cellulosic (cellulose, cellulose di- or tri-acetate, cellulose nitrate or blends thereof) membrane has hydroxyl moieties that are derivitized to form the charged surfaces. A wide variety of compounds can be used. Most possess a halide moiety capable of reacting with the membrane surface (including the interior of its pores) as well as a hydroxyl moiety capable of reacting with a second ligand that imparts the charge, positive or negative.

U.S. Pat. No. 4,824,568 teaches casting a polymeric coating onto a membrane's surface and then cross-linking it in place with UV light, electron beam or another energy source to input a charge to the membrane such as PVDF, polyethersulfone, polysulfone. PTFE resin and the like.

Other technologies such as polymerizing and crosslinking charged coatings or grafting charged materials onto the membrane surface can also be used.

Suitable membranes include but are not limited to polyethersulfone membranes such as BIOMAX® membranes, composite regenerated cellulose membranes such as Ultracel® membranes or regenerated cellulose membranes, such as PL membranes; all available from Millipore Corporation of Billerica, Mass.

The NMWCO for these membranes can be from about 0.5 kD to about 20 kD, preferably from about 1 kD to 10 kD. The size selected depends upon the molecule to be purified and/or concentrated, its charge, the level of charge that one is capable of applying to the membrane surfaces, whether the system is run as TFF, normal or the like, and the pressure under which the system is run.

In some instances, the repulsion effect can be enhanced by modifying the pH of the solution being filtered so as to cause the synthetic biomolecule or the membrane to have the same charge as the membrane or synthetic biomolecule. For example at neutral pH (pH=7), the molecule may have an opposite charge or a neutral charge. However, depending on its isoelectric point, raising or lowering the pH will cause the molecule to take on the same charge as the membrane. Likewise a membrane may have an opposite charge or a neutral charge. However, depending on its isoelectric point, raising or lowering the pH will cause the membrane to take on the same charge as the molecule to be separated.

What I claim:

1. A system for the purification by ultrafiltration of target synthetic biological molecules including oligonucleotides, synthetic DNA and synthetic RNA from a solution each molecule having a molecular weight from about 0.5 KD to less than 5 KD comprising:

a filtration holder having an inlet, a filtrate outlet and a retentate outlet, and a surface modified ultrafiltration membrane having a charged coating on the surface of the membrane, wherein the ultrafiltration membrane is located in the holder and separates the holder into an upstream compartment and a downstream compartment such that all filtrate must enter the inlet and pass through the surface modified ultrafiltration membrane before exiting the holder through the filtrate outlet, the surface modified ultrafiltration membrane has a nominal molecular weight cutoff (NMWCO) from about 0.5 KD to less than 5 KD when the modified membrane surface has a negative charge, or a nominal molecular weight cutoff (NMWCO) from about 0.5 KD to about 20 KD when the modified membrane surface has a positive charge;

wherein the NMWCO of the ultrafiltration membrane is larger than the molecular weight of the target synthetic biological molecules.

2. The system of claim 1 wherein the surface modified ultrafiltration membrane has a NMWCO from about 1 KD to less than about 4 KD and the modified membrane surface contains a negative charge.

3. The system of claim 1 wherein the surface modified ultrafiltration membrane has a NMWCO from about 1.5 KD to about 5 KD, the modified membrane surface contains a positive charge, and the membrane is a material selected from the group consisting of polyethersulfone, composite regenerated cellulose and regenerated cellulose.

4. The system of claim 1 further comprising a return loop in fluid communication between the retentate outlet and the inlet.

5. The system of claim 1 further comprising a pump upstream of the inlet.

6. The system of claim 1 further comprising a return loop in fluid communication between the retentate outlet and the inlet and a pump upstream of the inlet.

7. The system of claim 1 further comprising a return loop in fluid communication between the retentate outlet and the inlet, a pump upstream of the inlet and a second pump located in the return loop between the retentate outlet and the inlet.

8. The system of claim 1 further comprising a return loop in fluid communication between the retentate outlet and the inlet and a supply of retentate buffer in fluid communication with the return loop.

9. A method for purifying by ultrafiltration desired target synthetic biological molecules including oligonucleotides, synthetic DNA and synthetic RNA molecules each having a positive net charge from a source comprising:

supplying a source containing at least the desired positively charged target oligonucleotides, synthetic DNA and synthetic RNA molecules each having a molecular weight from about 0.5 KD to about 5 KD, providing a plurality of surface modified ultrafiltration membranes having a positive net charged coating on the surface of the membranes and the membranes have a NMWCO from about 0.5 KD to about 20 KD, wherein the NMWCO of each ultrafiltration membrane is larger than the molecular weight of the target synthetic biological molecules, filtering the source through the plurality of surface modified ultrafiltration membranes so as to obtain a retentate stream and a filtrate stream, and recovering the desired target oligonucleotides, synthetic DNA and synthetic RNA molecules from a stream selected from the group consisting of a retentate stream and a filtrate stream.

10. A method of claim 9 wherein the surface modified membranes have a NMWCO of from about 1 KD to less than 10 KD and are a material selected from the group consisting of polyethersulfone, composite regenerated cellulose and regenerated cellulose.

11. A method of claim 9 wherein the plurality of membranes have a NMWCO from about 1.5 KD to about 5 KD, and the membranes are a material selected from the group consisting of polyethersulfone, composite regenerated cellulose and regenerated cellulose.

12. A method of claim 9 further comprising a retentate recirculation loop and circulating the retentate through the loop and mixing the retentate with the source of oligonucleotides, synthetic DNA and synthetic RNA.

13. The method of claim 9 wherein the pH of the source is adjusted such that the desired target oligonucleotides, synthetic DNA and synthetic RNA molecules has a charge that is the same as the charge of the plurality of surface modified membranes.

14. The method of claim 9 wherein the pH of the source is adjusted such that the plurality of surface modified membranes has a charge that is the same as the charge of the desired target oligonucleotides, synthetic DNA and synthetic RNA molecules.

15. The method of claim 9 wherein the sieving value has at least a 1.5 fold improvement over that of a membrane of the same type having an uncharged membrane surface.

16. A method of separating a desired target oligonucleotides, synthetic DNA and synthetic RNA molecules having a molecular weight from about 0.5 KD to less than 5 KD from a solution containing a mixture of oligonucleotides, synthetic DNA and synthetic RNA molecules, impurities and a carrier fluid by normal flow filtration comprising the steps of:

providing a solution containing a mixture of oligonucleotides, synthetic DNA and synthetic RNA molecules, impurities and a carrier fluid, providing a plurality of surface modified ultrafiltration membranes having a charged coating on the surface of the membranes, the membranes having a NMWCO from about 0.5 KD to less than 5 KD when the plurality of membrane surfaces have negative charges, or a NMWCO from about 0.5 KD to about 20 KD when the plurality of membrane surfaces have positive charges, wherein the oligonucleotides, synthetic DNA and synthetic RNA molecules and plurality of surface modified membranes have like net charges, and the NMWCO of each ultrafiltration membrane is larger than the molecular weight of the target synthetic biological molecules, contacting the plurality of surface modified ultrafiltration membranes with the mixture under normal flow filtration, separating the desired oligonucleotides, synthetic DNA and synthetic RNA molecules from the mixture under normal flow filtration, retaining the desired oligonucleotides, synthetic DNA and synthetic RNA molecules upstream of the plurality of surface modified membranes, and passing under normal flow filtration the impurities, and carrier fluids through the plurality of surface modified membranes.

17. The method of claim 16 wherein the pH of the mixture is adjusted such that the desired target oligonucleotides, synthetic DNA and synthetic RNA molecules have a net charge that is the same as the net charge of the membrane.

18. The method of claim 16 wherein the pH of the mixture is adjusted such that the plurality of surface modified membranes have a charge that is the same as the charge of the desired target oligonucleotides, synthetic DNA and synthetic RNA molecules.

19. The method of claim 16 wherein the sieving value has at least a 1.5 fold improvement over that of a membrane of the same type having an uncharged membrane surface.

20. A system for the purification of positively charged target oligonucleotides, synthetic DNA and synthetic RNA molecules having a molecular weight from about 0.5 KD to about 5 KD by tangential flow filtration comprising:
- a filtration holder having,
  - an inlet,
  - a filtrate outlet,
  - a retentate outlet,
  - a first pump located upstream of the inlet,
  - a return loop in fluid communication between the retentate outlet and the inlet,
  - a supply of retentate buffer in fluid communication with the return loop,
  - a second pump located in the return loop between the retentate outlet and the inlet, and
    - a plurality of surface modified ultrafiltration membranes having a positively charged coating on the surface of the membranes, the membranes are located in the holder and separate the holder into an upstream compartment containing the retentate outlet and a downstream compartment containing the filtrate outlet such that all filtrate must enter the inlet and pass through, the plurality of surface modified membranes before exiting the holder through the filtrate outlet, the plurality of surface modified membranes having a nominal molecular weight cutoff (NMWCO) from about 0.5 KD to about 20 KD,
- wherein the NMWCO of each ultrafiltration membrane is larger than the molecular weight of the target synthetic biological molecules.

21. The system of claim 20 wherein the plurality of positively charged surface modified membranes have a NMWCO from about 1 KD to about 10 KD, and the membrane is a material selected from the group consisting of polyethersulfone, composite regenerated cellulose and regenerated cellulose.

22. The system of claim 20 wherein the plurality of positively charged surface modified membranes have a NMWCO from about 1.5 KD to about 5 KD, and the membrane is a material selected from the group consisting of polyethersulfone, composite regenerated cellulose or regenerated cellulose membranes.

23. A method for purifying desired positively charged target oligonucleotides, synthetic DNA and synthetic RNA molecules having a molecular weight from 0.5 KD to about 5 KD by tangential flow filtration comprising:
- supplying a source containing at least the desired target oligonucleotides, synthetic DNA and synthetic RNA molecules,
- providing a filtration holder having,
  - an inlet,
  - a first pump located upstream of the inlet,
  - a filtrate outlet,
  - a retentate outlet,
  - a return loop in fluid communication between the retentate outlet and the inlet,
  - a supply of retentate buffer in fluid communication with the return loop,
  - a second pump located in the return loop between the retentate outlet and the inlet, and
- providing a plurality of surface modified ultrafiltration membranes having a positively charged polymerized, crosslinked or grafted coating on the surface of the membranes, and the membranes have a NMWCO from about 0.5 KD to about 10 KD,
- wherein the NMWCO of each ultrafiltration membrane is larger than the molecular weight of the target synthetic biological molecules,
- filtering the source by tangential flow filtration through the plurality of positively charged surface modified ultrafiltration membranes so as to obtain a retentate stream and a filtrate stream, and
- recovering the desired positively charged target oligonucleotides, synthetic DNA and synthetic RNA molecules from the retentate stream.

24. The method of claim 23 wherein the plurality of positively charged surface modified membranes have a NMWCO from about 1 to about 10 KD, and the membrane is a material selected from the group consisting of polyethersulfone, composite regenerated cellulose or regenerated cellulose membranes.

25. The system of claim 23 wherein the plurality of positively charged surface modified membranes have a NMWCO from about 1.5 to about 5 KD, and the membrane is a material selected from the group consisting of polyethersulfone, composite regenerated cellulose or regenerated cellulose membranes.

26. A system for the purification of positively charged target oligonucleotides, synthetic DNA and synthetic RNA molecules having a molecular weight from about 0.5 KD to less than 5 KD by tangential flow filtration comprising:
- a filtration holder having,
  - an inlet,
  - a filtrate outlet,
  - a retentate outlet,
  - a first pump located upstream of the inlet,
  - a return loop in fluid communication between the retentate outlet and the inlet,
  - a supply of retentate buffer in fluid communication with the return loop,
  - a second pump located in the return loop between the retentate outlet and the inlet, and
- a plurality of surface modified ultrafiltration membranes having a positively charged coating on the surface of the membranes, the membranes are located in the holder and separate the holder into an upstream compartment containing the retentate outlet and a downstream compartment containing the filtrate outlet such that all filtrate must enter the inlet and pass through the plurality of surface modified membranes before exiting the holder through the filtrate outlet, the plurality of surface modified membranes having a nominal molecular weight cutoff (NMWCO) from about 1.5 KD to about 5 KD and the membrane is a material selected from the group consisting of polyethersulfone, composite regenerated cellulose or regenerated cellulose membranes,
- wherein the NMWCO of each ultrafiltration membrane is larger than the molecular weight of the target synthetic biological molecules.

27. A method for purifying desired positively charged target oligonucleotides, synthetic DNA and synthetic RNA molecules having a molecular weight from about 0.5 KD to less than 5 KD by tangential flow filtration comprising:
- supplying a source containing at least the desired target oligonucleotides, synthetic DNA and synthetic RNA molecules,
- providing a filtration holder having,
  - an inlet,
  - a first pump located upstream of the inlet, a filtrate outlet, a retentate outlet, a return loop in fluid communication between the retentate outlet and the inlet, a supply of retentate buffer in fluid communication with the return loop, a second pump located in the return loop between the retentate outlet and the inlet, and providing a plurality of surface modified ultrafiltration membranes having a positively charged polymerized, crosslinked or grafted coating on the surface of the membranes, and the membranes have a NMWCO from about 1.5 KD to about 5 KD and the membranes are selected from the group consisting of polyethersulfone, composite regenerated cellulose or regenerated cellulose membranes, wherein the NMWCO of each ultrafiltration membrane is larger than the molecular weight of the target synthetic biological molecules, filtering the source by tangential flow filtration through the plurality of positively charged surface modified ultrafiltration membranes so as to obtain a retentate stream and a filtrate stream, and recovering the desired positively charged target oligonucleotides, synthetic DNA and synthetic RNA molecules from the retentate stream.

* * * * *

UNITED STATES PATENT AND TRADEMARK OFFICE
CERTIFICATE OF CORRECTION

PATENT NO. : 8,075,780 B2  
APPLICATION NO. : 10/981328  
DATED : December 13, 2011  
INVENTOR(S) : Richard James Pearce Page 1 of 1

It is certified that error appears in the above-identified patent and that said Letters Patent is hereby corrected as shown below:

On title page, item 56, under "FOREIGN PATENT DOCUMENTS", in column 2, line 5, delete "1998/015681" and insert -- 1988/015581 --, therefor.

On title page, item 57, under "ABSTRACT", in column 2, line 2, delete "cut off" and insert -- cutoff --, therefor.

In column 5, line 55, in claim 9, delete "20 KD ," and insert -- 20 KD, --, therefor.

In column 7, line 27, in claim 20, delete "through," and insert -- through --, therefor.

In column 7, line 55, in claim 23, delete "holderhaving," and insert -- holder having, --, therefor.

Signed and Sealed this
Twenty-ninth Day of May, 2012

David J. Kappos
*Director of the United States Patent and Trademark Office*